(12) United States Patent
Vinik et al.

(10) Patent No.: US 6,986,994 B2
(45) Date of Patent: Jan. 17, 2006

(54) INGAP DISPLACEMENT ASSAYS

(75) Inventors: Aaron I. Vinik, Norfolk, VA (US); David A. Taylor-Fishwick, Norfolk, VA (US)

(73) Assignee: GMP Endotherapeutics, Inc., Fort Lauderdale, FL (US)

(*) Notice: Subject to any disclaimer, the term of this patent is extended or adjusted under 35 U.S.C. 154(b) by 630 days.

(21) Appl. No.: 10/036,418

(22) Filed: Jan. 7, 2002

(65) Prior Publication Data

US 2002/0127624 A1 Sep. 12, 2002

Related U.S. Application Data (60) Provisional application No. 60/260,210, filed on Jan. 9, 2001.

(51) Int. Cl.
 *G01N 33/53* (2006.01)

(52) U.S. Cl. ............... 435/7.1; 435/7.4; 435/7.5; 435/7.92; 435/7.93; 436/15; 436/43; 436/514; 436/543; 436/544; 436/545; 436/546

(58) Field of Classification Search .......... 435/7.1, 435/7.4, 7.5, 7.93, 7.92; 436/15, 43, 514, 436/543–546
See application file for complete search history.

(56) References Cited

U.S. PATENT DOCUMENTS 5,804,421 A 9/1998 Vinik et al.
5,834,590 A 11/1998 Vinik et al.
5,840,531 A 11/1998 Vinik et al.

*Primary Examiner*—Long V. Le
*Assistant Examiner*—Jacob Cheu
(74) *Attorney, Agent, or Firm*—Lott & Friedland, P.A.; Michael J. Keller (57) ABSTRACT

An antibody is provided which specifically recognizes and binds to INGAP protein. The antibody is used in competitive binding assays for quantitation of INGAP in biological samples. The assay can be performed on a solid support or in a suspension.

14 Claims, 6 Drawing Sheets

INGAP Displacement ELISA

Peptide regions of INGAP

- ◉ INGAP[20-40]
- ○ INGAP[104-118]
- ● INGAP[140-152]
- ◉ INGAP[151-164]

Figure 6

INGAP DISPLACEMENT ASSAYS

This application claims the benefit of provisional application U.S. Ser. No. 60/260,210 filed Jan. 9, 2001.

TECHNICAL FIELD OF THE INVENTION

The invention relates to the field of clinical and analytical assays of biological products. In particular it relates to the field of immunoassays.

BACKGROUND OF THE INVENTION

Islet neogenesis associated protein (INGAP) is a product of a gene expressed in regenerating hamster pancreas. INGAP gene is expressed in acinar cells, but not in islets. Western blot analysis demonstrates the presence of INGAP in Ilotropin, a protein extract isolated from cellophane wrapped pancreata, but not in extracts from control pancreata. A synthetic pentadecapeptide, corresponding to a region unique to INGAP, stimulates a 2.4-fold increase in [3H]thymidine incorporation into hamster duct epithelium in primary culture and a rat pancreatic duct cell line but has no effect on a hamster insulinoma tumor cell line. A portion of human INGAP gene has been cloned and appears to be highly homologous to the hamster gene. INGAP gene is a pancreatic gene expressed during islet neogenesis whose protein product is a constituent of Ilotropin and is capable of initiating duct cell proliferation, a prerequisite for islet neogenesis. J Clin Invest 1997 May 1; 99(9):2100–9. There is a need in the art for tools for measuring INGAP to enable and facilitate the full exploitation of this important protein for fighting human disease, such as diabetes types I and II.

SUMMARY OF THE INVENTION

It is an object of the invention to provide methods for assaying INGAP protein in a test sample.

It is an object of the invention to provide antibodies for assaying INGAP protein in a test sample.

One or more of the following embodiments provides these and other objects of the invention. In one embodiment of the invention a method is provided for assaying INGAP in a test sample. A solid support comprising bound antibodies is contacted with a test sample. The antibodies specifically bind to an amino acid sequence FLSWVEGEESQKKLPSSRITC (SEQ ID NO: 1) of INGAP protein. INGAP protein in the test sample binds to the solid support. Test sample which has not bound to the solid support is removed. The solid support is contacted with a quantity of a labeled INGAP molecule such that all or a portion of the quantity of labeled INGAP molecule binds to the solid support. Labeled INGAP molecule which has not bound to the solid support is removed. The amount of labeled INGAP molecule bound to the solid support is determined. Labeled INGAP molecule bound to the solid support is inversely related to INGAP protein in the test sample.

According to another embodiment of the invention a method is provided for assaying INGAP in a test sample. Antibodies which specifically bind to an amino acid sequence FLSWVEGEESQKKLPSSRITC (SEQ ID NO: 1) of INGAP protein are contacted with a test sample which may contain INGAP protein, and a labeled INGAP molecule. The amount of labeled INGAP molecule bound to the antibodies is determined. The amount of labeled INGAP molecule bound to the antibodies is inversely related to INGAP protein in the test sample.

According to another embodiment of the invention an isolated antibody is provided which specifically binds to an amino acid sequence FLSWVEGEESQKKLPSSRITC as shown in SEQ ID NO: 1.

These and other embodiments of the invention which are described in more detail below, provide the art with a quantitative means of determining INGAP in culture media, biological tissues, and in biological fluids.

DETAILED DESCRIPTION OF THE INVENTION

It is a discovery of the present invention that antibodies directed to a particular portion of INGAP are able to bind to full-length INGAP and provide a reliable means of quantitation of INGAP in biological samples The antibodies are specific for the particular portion of INGAP and other portions do not effectively compete for antibody binding.

The peptide immunogen FLSWVEGEESQKKLPSSRITC (SEQ ID NO: 1) consists of residue numbers 20–40 of full length INGAP protein. While applicants do not wish to be bound by any particular theory, it is believed that this portion is suitable because of its uniqueness to INGAP. Thus it is believed that other subfragments or overlapping fragments of at least 6, 8, 10, 12, or 14 contiguous amino acids up to about 30 amino acids would be useful. Applicants note that a peptide consisting of residues 104–118 did not successfully compete with full length INGAP for binding to the antibodies.

Assays of the invention can be performed in solution/suspension or on a solid support. Suitable solid supports include without limitation: microtiter dishes, filters, nylon, membranes, plastics, column packing materials, beads. Typically antibodies are applied to a surface in a liquid and the liquid is removed by drying. Alternatively, solid substrate or support can be derivatized to covalently bind to the antibodies. Such techniques are known in the art and can be selected as is convenient by one of ordinary skill in the art.

Test samples can be samples from cells, tissues, organs, or bodily fluids of a human or other test mammal. Samples can also be fermentation broths, or cell lysates from recombinant or natural cells which produce INGAP. Samples can be pretreated to remove fractions which do not contain INGAP. This can be done by specifically removing other components or by purifying and selecting for INGAP in samples.

Antibodies employed preferably have been produced by immunizing with a peptide according to SEQ ID NO: 1: FLSWVEGESQKKLPSSRITC. However, any peptide having at least six of such contiguous amino acids can be useful. Thus the following peptides or polypeptides containing such peptides can be contemplated as immunogens.

FLSWVE (SEQ ID NO: 5)
LSWVEG (SEQ ID NO: 6)
SWVEGE (SEQ ID NO: 7)
WVEGES (SEQ ID NO: 8)
VEGESQ (SEQ ID NO: 9)
EGESQK (SEQ ID NO: 10)
GESQKK (SEQ ID NO: 11)
ESQKKL (SEQ ID NO: 12)
SQKKLP (SEQ ID NO: 13)
QKKLPS (SEQ ID NO: 14)
KKLPSS (SEQ ID NO: 15)
KLPSSR (SEQ ID NO: 16)
LPSSRI (SEQ ID NO: 17)
PSSRIT (SEQ ID NO: 18)
SSRITC (SEQ ID NO: 19)

Peptides can be parts of larger molecules. For example, protein adjuvants such as keyhole limpet hemocyanin can be conjugated to peptides to enhance immunogenicity. Antibodies can be polyclonal or monoclonal. They can be produced by any technology known in the art, including hybridomas, cloning, and phage display. Antibodies can be screened and selected and purified as desired using any technique known in the art. They can be produced in humans, goats, rabbits, mice, etc. They can be the product of an antibody encoded by any species, whether produced in that species or a heterologous species.

The assay of the present invention is a competitive assay in which unlabeled analyte (INGAP) in a sample competes with a labeled analyte for binding to the antibody. The labeled analyte can be full-length INGAP or an appropriate INGAP peptide which binds to the antibody. The labeled analyte can be, e.g. radiolabeled, fluorescently labeled, or enzymatically labeled. The label can be covalently attached to the analyte or can be attached via a strong binding interaction, e.g., avidin/biotin.

Other peptide sequences can be used in place of residues 20–40 of INGAP. These include peptides comprising residues 104–118 (IGLHDPSHGTLPNGS; SEQ ID NO:2), 139–152 (IAADRGYCAVLSQK; SEQ ID NO:3), and 151–164 (QKSGFQKWRDFNCE; SEQ ID NO:4). As stated above, subfragments of as little as six residues can be used as immunogens, and can be fused or conjugated other proteins or adjuvant molecules. Use of such peptides requires use of the corresponding antibody in the assay.

EXAMPLES

I. General Methodology:

INGAP specific antibody is coated at the required concentration onto a solid matrix. Following coating, the matrix is washed twice and remaining non-specific protein binding sites blocked by incubation in an appropriate blocking buffer. The matrix is washed in a wash buffer and samples or standards to be assayed are incubated with the matrix. Washing of the matrix removes unbound INGAP and the remaining exposed antibody sites are probed by incubating the matrix with an INGAP reporter construct (details below). Quantitation of the INGAP reporter construct is achieved with an appropriate detection technique. Displacement of signal provides a measure of INGAP in test material.

III. Details of the Current Assay:

50:1 of INGAP(residues 20–40) antibody in PBS is added to wells of a 96 well flat bottom MAXISORB™ plate (NUNC). To control wells is added 50:1 of PBS. The plate is incubated at 37° C. in a dry incubator for 3 hrs. Each well of the plate is washed twice with 200:1 of PBS and tapped dry before being filled with 300:1 of 2% BSA-PBS and incubated overnight at 4° C. to block free protein binding sites in each well. After the overnight incubation each well of the plate is washed twice with 200:1 of PBS before up to 200:1 of sample or known dilutions of rINGAP or INGAP-peptide is added to the appropriate wells. The highest dilution of the known protein is also added to the wells that were not coated with anti-INGAP(residues 20–40). The samples are left to bind for 2 hours at 37° C. in a dry incubator. The contents of each well is removed and the wells washed thrice in HBHA buffer (Hank's balance salt solution, 0.5 mg/ml BSA, 0.1% NaN3, 20 mM HEPES, pH7.0) before the addition of 100:1 of culture supernatant from INGAP-fusion protein-expressing cells. Following a further incubation at 37° C. for 90 min. the wells were washed thrice with 200:1 of HBHA and tapped dry. The amount of INGAP fusion protein bound in each well was determined by the addition to each well of 100:1 of chromogenic substrate for the fusion protein. The development of color is determined by reading the absorbance of each well. The displacement of signal obtained using the known concentrations of INGAP (or peptide) is used to generate a standard curve in an excel spreadsheet from which INGAP concentrations in the samples are calculated.

IV. Generation of INGAP Fusion Proteins:

Cloned INGAP cDNA was subjected to PCR using 3' and 5' primers which introduced desired restriction sites 3' and 5' respectively to allow the insertion of INGAP into cloning vectors in the correct reading frame to form fusion proteins. Restriction digestion of the vector and PCR adjusted INGAP genes followed by ligation of the purified products, resulted in INGAP fusion constructs.

IV.1 INGAP-Fusion Protein with Enzyme

Cloned INGAP gene was subject to PCR using the 3' primer (5'GCGAAGATCTGACCTTGAATTTGCAGAT3'; SEQ ID NO: 20) and 5' primer (5'CGCCCAAGCTTACCATGATGCTTCCCATGACCCTC3'; SEQ ID NO: 21) which introduced the restriction sites BglII and HindIII 3' and 5' respectively onto the INGAP gene. This allowed the insertion of INGAP into a vector in the correct reading frame. Restriction digestion of the vector and PCR adjusted INGAP with BglII and HindIII was followed by ligation of the purified products. The resulting vector expresses the fusion protein.

IV.2 INGAPMAT Fusion Protein with Enzyme

Cloned INGAP gene without the signal sequence (INAGPMAT) was subjected to PCR using the 3' primer (5'GCCGCTCGAGCTAGACCTTGAATTTGCAGAT3'; SEQ ID NO: 22) and 5' primer (5'GCCGAAGATCTGAAGAATCTCAAAAGAAACTG3'; SEQ ID NO: 23) which introduced the restriction sites XhoI and BglII 3' and 5' respectively onto the INGAPMAT gene. This allowed the insertion of INGAPMAT into a vector in the correct reading frame. Restriction digestion of the vector and PCR adjusted INGAPMAT with XhoI and BglII was followed by ligation of the purified products. The resulting vector expresses the fusion construct.

IV.3 INGAP Peptide Fusion with Enzyme

Cloned INGAP gene was subjected to PCR using the 3' primer (5' GCCGCTCGAGCTAACTTCCGTTGGGTAGTGTACC3'; SEQ ID NO: 24) and 5' primer (5'GCCGAAGATCTATTGGACTCCATGATCCCTCA3';

SEQ ID NO: 25)) which introduced the restriction sites XhoI and BglII 3' and 5' respectively onto a partial sequence the INGAP gene. This allowed the insertion of INGAP peptide 104–118 into the vector in the correct reading frame. Restriction digestion of the vector and PCR adjusted INGAP with XhoI and BglII was followed by ligation of the purified products. The resulting vector expresses the fusion construct comprising marker protein and INGAP peptide 104–118.

IV.4 INGAP Fusion

Cloned INGAP gene was subjected to PCR using the 3' primer (5'CGCCCAAGCTTGACCTTGAATTTGCAGAT3'; SEQ ID NO: 26) and 5' primer (5'GCCGAAGATCTATGAT GCTTCCCATGACCCTC3'; SEQ ID NO: 27) which introduced the restriction sites XhoI and BglII 3' and 5' respectively onto the INGAP gene. This allowed the insertion of INGAP into the vector in the correct reading frame. Restriction digestion of the vector and PCR adjusted INGAP with XhoI and BglII was followed by ligation of the purified products. The resulting vector expresses the fusion construct of INGAP and a fluorescent marker protein.

V. Production of INGAP Fusion Proteins

Using lipofectamine (Gibco BRL), 10: g of the INGAP-fusion protein expression vector was transiently transfected into 293T cells. At time intervals following transfection the culture supernatant was harvested from the cells and assayed for INGAP fusion protein expression. Either purified concentrates, or dilutions, of the expressed fusion protein are used in INGAP detection assays.

Example 1

Figure 1:
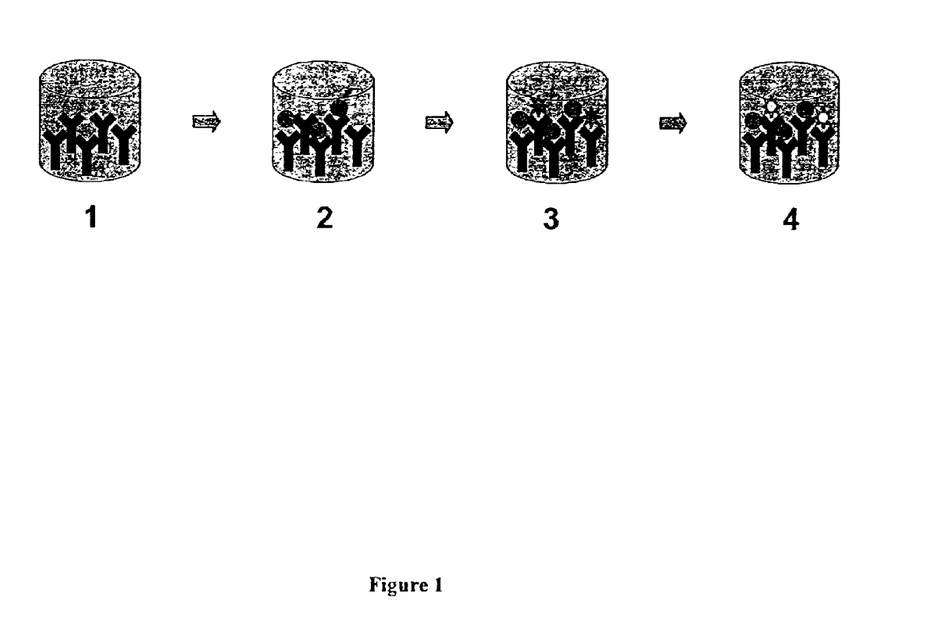
FIG. 1 is a schematic of an assay according to the present invention. INGAP detection antibody which is specifically immunoreactive with INGAP residues 20–40 can be attached to a solid support. A sample which contains INGAP is contacted with the solid support and the antibodies capture the INGAP. Unoccupied INGAP-binding sites on the solid support are then contacted with and occupied by a tagged INGAP molecule. The amount of tagged INGAP molecules captured on the solid support is determined, from which the amount of untagged INGAP in the test sample is calculated.
Figure 2:
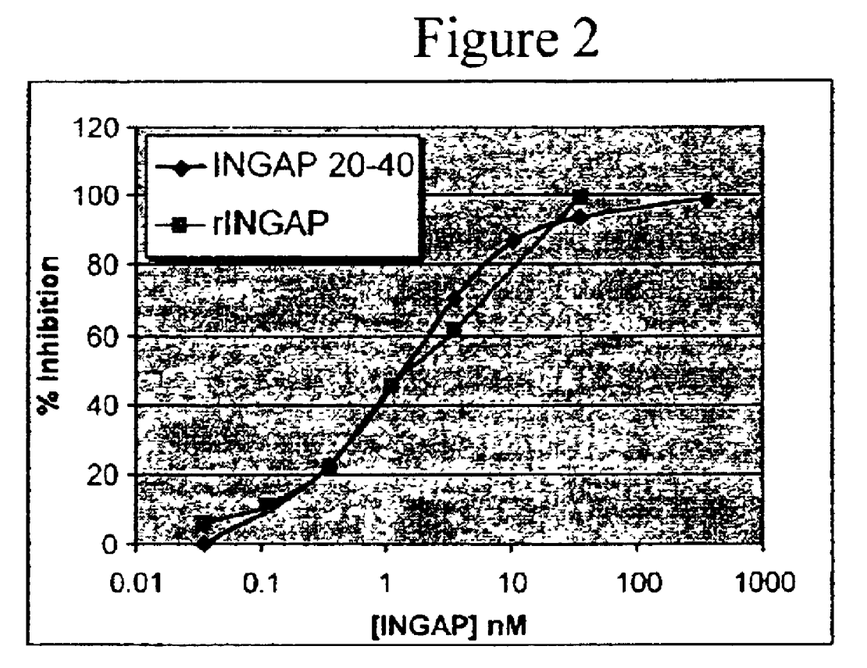
FIG. 2 shows a dose displacement curve using INGAP peptide (residues 20–40; "INGAP-LY") and recombinant INGAP.
Figure 3:
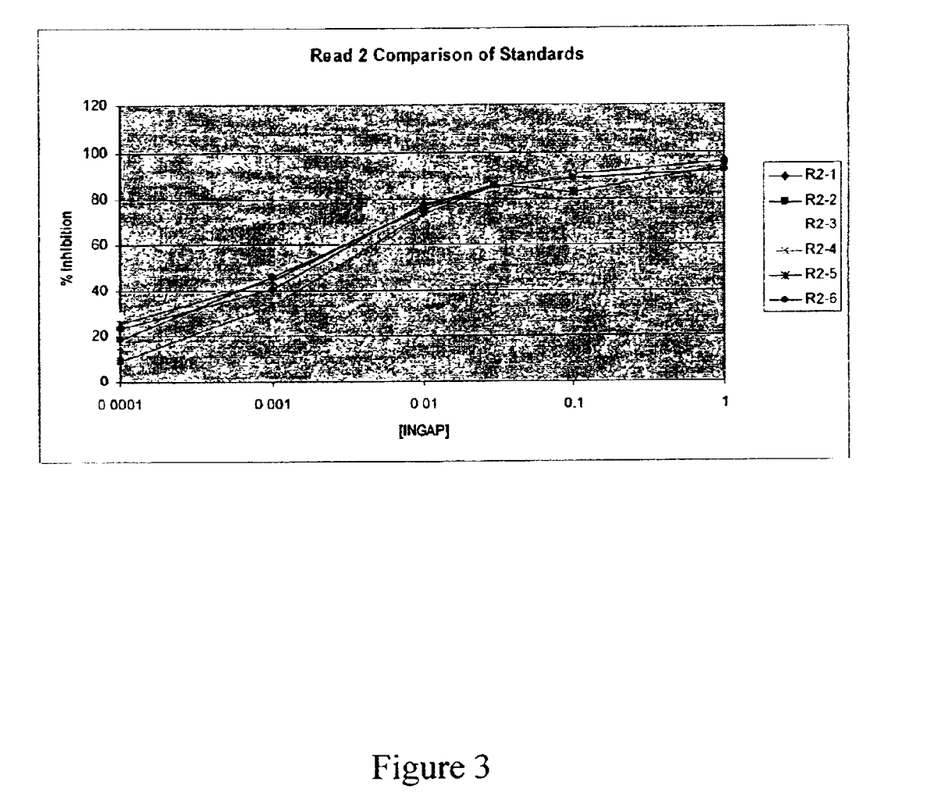
FIG. 3 shows reproducible peptide displacement curves for six individual determinations of standards.
Figure 4:
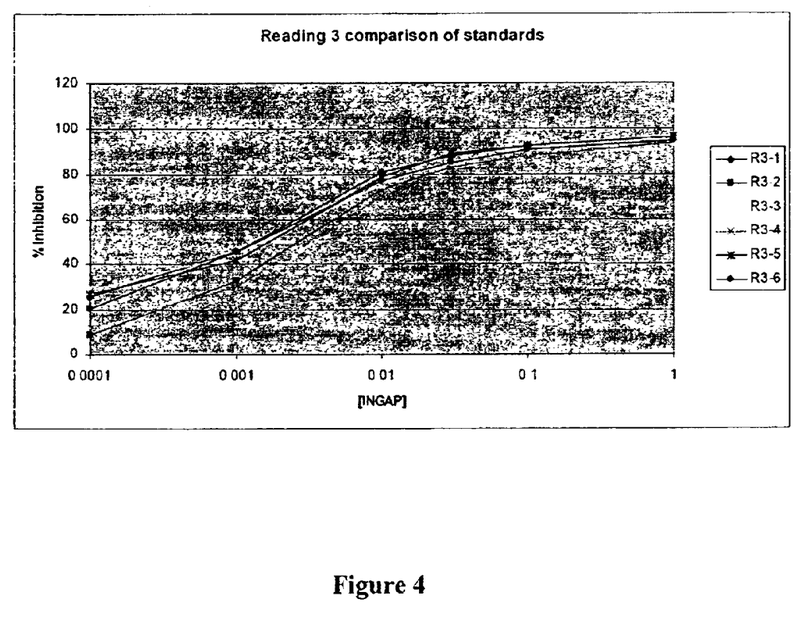
FIG. 4 shows reproducible peptide displacement curves for six individual determinations of standards at a later time point than in FIG. 3.

By using known concentrations of the INGAP peptide (residues 20–40) a dose displacement curve was generated and the data generated subsequently transformed to display percentage inhibition. FIG. 2. The curve clearly displays dose-dependant saturable-binding. Test dilutions of a recombinant INGAP were assayed to determine the actual concentration of recombinant INGAP in the preparation. Using the INGAP 20–40 peptide curve the equivalent molar concentration of recombinant INGAP and INGAP 20–40 peptide was determined. The curves shown are superimposed at their calculated molar concentrations. These data provide an accurate determination of recombinant INGAP concentration.

Example 2

Figure 5:
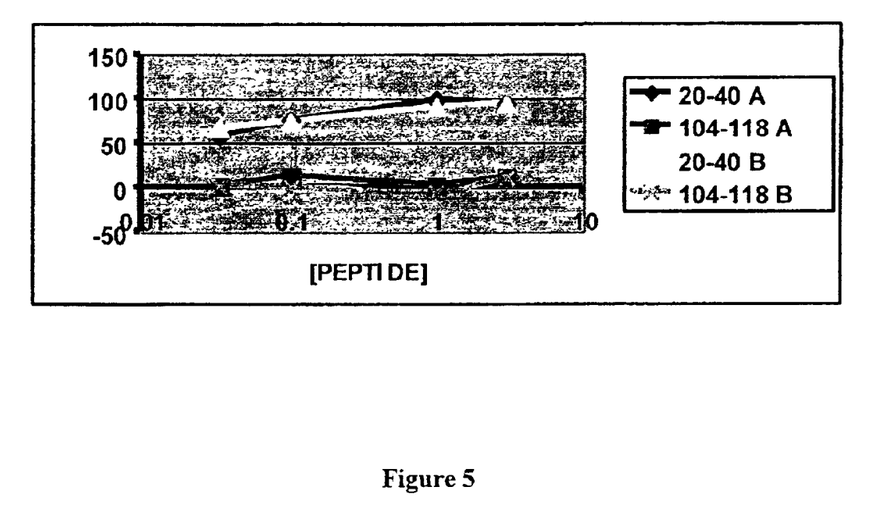
FIG. 5 shows the specificity of the assay. A peptide from a distinct region of INGAP (residues 104–118) was used as the tagged INGAP molecule.
Figure 6:
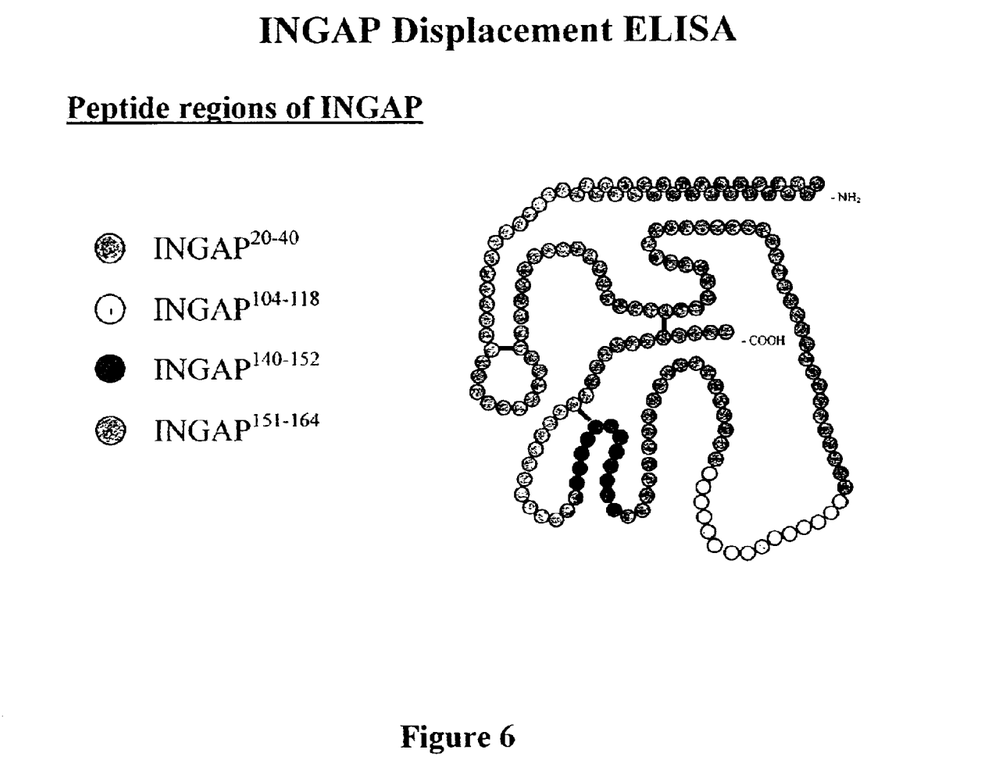
FIG. 6 shows peptide regions of INGAP schematically.

INGAP 20–40 and INGAP 114–118 were compared in their ability to compete for binding to the antibodies of the invention. FIG. 5 shows that only INGAP 20–40 functions in this assay. The assay was performed at two antibody coating concentrations, 7 and 10 ug/ml, to explore further the potential for non-specific interactions.

We claim:

1. A method for assaying islet neogenesis associated protein (INGAP) molecule in a test sample, comprising:
   a. contacting a solid support comprising bound antibodies with a test sample, wherein the antibodies specifically bind to an amino acid sequence FLSWVEGEESQKKLPSSRITC (SEQ ID NO: 1) of INGAP molecule, whereby INGAP molecule in the test sample binds to the antibodies and thereby to the solid support;
   b. removing the test sample which has not bound to the antibodies and thereby not bound to the solid support;
   c. contacting the solid support with a quantity of a labeled INGAP molecule, whereby all or a portion of the quantity of labeled INGAP molecule binds to the antibodies and thereby to the solid support;
   d. removing labeled INGAP molecule which has not bound to the antibodies and thereby not bound to the solid support; and
   e. determining the amount of labeled INGAP molecule bound to the solid support wherein the amount of labeled INGAP molecule bound to the antibodies and thereby to the solid support is inversely related to the amount of INGAP molecule in the test sample.

2. The method of claim 1 further comprising:
   a. generating a standard curve using a series of control samples having known quantities of labeled INGAP molecule; and
   b. comparing the amount of labeled INGAP molecule bound to the antibodies and thereby to the solid support in presence of the test sample to the standard curve, whereby the amount of INGAP molecule in the test sample is determined.

3. The method of claim 1 wherein the labeled INGAP molecule comprises a fusion protein comprising INGAP molecule and a marker protein.

4. The method of claim 3 wherein the marker protein is enzymatically active.

5. The method claim 3 wherein the marker protein is fluorescent.

6. The method of claim 4 wherein a chromogenic substrate is contacted with the marker protein to determine the amount of marker to the solid support.

7. The method of claim 1 wherein the labeled INGAP molecule is radioactively labeled.

8. A method for assaying islet neogenesis associated protein (INGAP) molecule in a test sample, comprising: contacting
   a. antibodies which specifically bind to an amino acid sequence FLSWVEGEESQKKLPSSRITC (SEQ ID NO: 1) of INGAP molecule,
   b. a test sample which may contain INGAP molecule, and
   c. a labeled INGAP molecule; and
determining the amount of labeled INGAP molecule bound to the antibodies, wherein the amount of labeled INGAP molecule bound to the antibodies is inversely related to the amount of INGAP molecule in the test sample.

9. The method of claim 8 wherein the labeled INGAP molecule is a fusion protein comprising INGAP molecule and a marker protein.

10. The method of claim 8 further comprising:
    a. generating a standard curve using a series of control samples having known quantities of INGAP molecule; and
    b. comparing the amount of labeled INGAP molecule bound to the solid support in presence of the test sample to the standard curve, whereby an amount of INGAP molecule in the test sample is determined.

11. The method of claim 8 wherein prior to the step of determining the amount of labeled INGAP molecule bound to the antibodies, the antibodies are separated from components which are not specifically bound to the antibodies.

12. The method of claim 9 wherein the marker protein is enzymatically active.

13. The method of claim 9 wherein the marker protein is fluorescent.

14. The method of claim 12 wherein a chromogenic substrate is contacted with the marker protein to determine the amount of marker protein bound to the antibodies.

* * * * *

SEQUENCE LISTING

```
<160> NUMBER OF SEQ ID NOS: 27

<210> SEQ ID NO 1
<211> LENGTH: 21
<212> TYPE: PRT
<213> ORGANISM: Cricetulus

<400> SEQUENCE: 1

Phe Leu Ser Trp Val Glu Gly Glu Glu Ser Gln Lys Lys Leu Pro Ser
1               5                   10                  15

Ser Arg Ile Thr Cys
            20

<210> SEQ ID NO 2
<211> LENGTH: 15
<212> TYPE: PRT
<213> ORGANISM: Cricetulus

<400> SEQUENCE: 2

Ile Gly Leu His Asp Pro Ser His Gly Thr Leu Pro Asn Gly Ser
1               5                   10                  15

<210> SEQ ID NO 3
<211> LENGTH: 14
<212> TYPE: PRT
<213> ORGANISM: Cricetulus

<400> SEQUENCE: 3

Ile Ala Ala Asp Arg Gly Tyr Cys Ala Val Leu Ser Gln Lys
1               5                   10

<210> SEQ ID NO 4
<211> LENGTH: 14
<212> TYPE: PRT
<213> ORGANISM: Cricetulus
```

-continued

```
<400> SEQUENCE: 4

Gln Lys Ser Gly Phe Gln Lys Trp Arg Asp Phe Asn Cys Glu
 1               5                  10

<210> SEQ ID NO 5
<211> LENGTH: 6
<212> TYPE: PRT
<213> ORGANISM: Cricetulus

<400> SEQUENCE: 5

Phe Leu Ser Trp Val Glu
 1               5

<210> SEQ ID NO 6
<211> LENGTH: 6
<212> TYPE: PRT
<213> ORGANISM: Cricetulus

<400> SEQUENCE: 6

Leu Ser Trp Val Glu Gly
 1               5

<210> SEQ ID NO 7
<211> LENGTH: 6
<212> TYPE: PRT
<213> ORGANISM: Cricetulus

<400> SEQUENCE: 7

Ser Trp Val Glu Gly Glu
 1               5

<210> SEQ ID NO 8
<211> LENGTH: 6
<212> TYPE: PRT
<213> ORGANISM: Cricetulus

<400> SEQUENCE: 8

Trp Val Glu Gly Glu Ser
 1               5

<210> SEQ ID NO 9
<211> LENGTH: 6
<212> TYPE: PRT
<213> ORGANISM: Cricetulus

<400> SEQUENCE: 9

Val Glu Gly Glu Ser Gln
 1               5

<210> SEQ ID NO 10
<211> LENGTH: 6
<212> TYPE: PRT
<213> ORGANISM: Cricetulus

<400> SEQUENCE: 10

Glu Gly Glu Ser Gln Lys
 1               5

<210> SEQ ID NO 11
<211> LENGTH: 6
<212> TYPE: PRT
<213> ORGANISM: Cricetulus

<400> SEQUENCE: 11
```

```
Gly Glu Ser Gln Lys Lys
  1               5

<210> SEQ ID NO 12
<211> LENGTH: 6
<212> TYPE: PRT
<213> ORGANISM: Cricetulus

<400> SEQUENCE: 12

Glu Ser Gln Lys Lys Leu
  1               5

<210> SEQ ID NO 13
<211> LENGTH: 6
<212> TYPE: PRT
<213> ORGANISM: Cricetulus

<400> SEQUENCE: 13

Ser Gln Lys Lys Leu Pro
  1               5

<210> SEQ ID NO 14
<211> LENGTH: 6
<212> TYPE: PRT
<213> ORGANISM: Cricetulus

<400> SEQUENCE: 14

Gln Lys Lys Leu Pro Ser
  1               5

<210> SEQ ID NO 15
<211> LENGTH: 6
<212> TYPE: PRT
<213> ORGANISM: Cricetulus

<400> SEQUENCE: 15

Lys Lys Leu Pro Ser Ser
  1               5

<210> SEQ ID NO 16
<211> LENGTH: 6
<212> TYPE: PRT
<213> ORGANISM: Cricetulus

<400> SEQUENCE: 16

Lys Leu Pro Ser Ser Arg
  1               5

<210> SEQ ID NO 17
<211> LENGTH: 6
<212> TYPE: PRT
<213> ORGANISM: Cricetulus

<400> SEQUENCE: 17

Leu Pro Ser Ser Arg Ile
  1               5

<210> SEQ ID NO 18
<211> LENGTH: 6
<212> TYPE: PRT
<213> ORGANISM: Cricetulus

<400> SEQUENCE: 18

Pro Ser Ser Arg Ile Thr
```

<210> SEQ ID NO 19
<211> LENGTH: 6
<212> TYPE: PRT
<213> ORGANISM: Cricetulus

<400> SEQUENCE: 19

Ser Ser Arg Ile Thr Cys
 1               5

<210> SEQ ID NO 20
<211> LENGTH: 28
<212> TYPE: DNA
<213> ORGANISM: Artificial Sequence
<220> FEATURE:
<223> OTHER INFORMATION: PCR primer

<400> SEQUENCE: 20
gcgaagatct gaccttgaat ttgcagat                                          28

<210> SEQ ID NO 21
<211> LENGTH: 35
<212> TYPE: DNA
<213> ORGANISM: Artificial Sequence
<220> FEATURE:
<223> OTHER INFORMATION: PCR primer

<400> SEQUENCE: 21
cgcccaagct taccatgatg cttcccatga ccctc                                  35

<210> SEQ ID NO 22
<211> LENGTH: 31
<212> TYPE: DNA
<213> ORGANISM: Artificial Sequence
<220> FEATURE:
<223> OTHER INFORMATION: PCR primer

<400> SEQUENCE: 22
gccgctcgag ctagaccttg aatttgcaga t                                      31

<210> SEQ ID NO 23
<211> LENGTH: 32
<212> TYPE: DNA
<213> ORGANISM: Artificial Sequence
<220> FEATURE:
<223> OTHER INFORMATION: PCR primer

<400> SEQUENCE: 23
gccgaagatc tgaagaatct caaaagaaac tg                                     32

<210> SEQ ID NO 24
<211> LENGTH: 34
<212> TYPE: DNA
<213> ORGANISM: Artificial Sequence
<220> FEATURE:
<223> OTHER INFORMATION: PCR primer

<400> SEQUENCE: 24
gccgctcgag ctaacttccg ttgggtagtg tacc                                   34

<210> SEQ ID NO 25
<211> LENGTH: 32
<212> TYPE: DNA
<213> ORGANISM: Artificial Sequence
<220> FEATURE:

-continued

```
<223> OTHER INFORMATION: PCR primer

<400> SEQUENCE: 25
gccgaagatc tattggactc catgatccct ca                              32

<210> SEQ ID NO 26
<211> LENGTH: 29
<212> TYPE: DNA
<213> ORGANISM: Artificial Sequence
<220> FEATURE:
<223> OTHER INFORMATION: PCR primer

<400> SEQUENCE: 26
cgcccaagct tgaccttgaa tttgcagat                                  29

<210> SEQ ID NO 27
<211> LENGTH: 32
<212> TYPE: DNA
<213> ORGANISM: Artificial Sequence
<220> FEATURE:
<223> OTHER INFORMATION: PCR primer

<400> SEQUENCE: 27
gccgaagatc tatgatgctt cccatgaccc tc                              32
```